United States Patent [19]
DasGupta et al.

[11] Patent Number: 5,658,947
[45] Date of Patent: Aug. 19, 1997

[54] METHOD AND COMPOSITION FOR SELECTIVELY INHIBITING MELANOMA USING BETALINIC ACID

[75] Inventors: Tapas K. DasGupta; John M. Pezzuto, both of River Forest, Ill.

[73] Assignee: Board of Trustees of the University of Illinois, Urbana, Ill.

[21] Appl. No.: 407,756

[22] Filed: Mar. 21, 1995

[51] Int. Cl.⁶ .................................................. A61K 31/22

[52] U.S. Cl. .......................... 514/510; 514/554; 514/570; 514/572; 514/573; 514/621; 514/623; 514/661; 514/703

[58] Field of Search .................................. 514/510, 570, 514/621, 554, 572, 573, 623, 661, 703

[56] References Cited

U.S. PATENT DOCUMENTS 5,468,888  11/1995  Bouboutou et al. ...................... 554/58

OTHER PUBLICATIONS

Derwent Abstracts 89–204083/28, "Carcinostatics Containing Betulin Derivatives" Dec. 1987.
Chemical Abstracts 116:277, "Sterol and Triterpene Derivatives From Plants Inhibit the Effects of a Tumor Promoter" 1991.
Chemical Abstracts 112:125164, "Content of Betulin and Betulinic Acid, Antitumor Agents of Zizyphus Species" 1989.

Primary Examiner—Frederick Krass
Attorney, Agent, or Firm—Marshall, O'Toole, Gerstein, Murray & Borun

[57] ABSTRACT

A composition and method of inhibiting tumor growth and treating malignant melanoma without toxic side effects are disclosed. Betulinic acid or a betulinic acid derivative is the active compound of the composition, which is topically applied to the situs of tumor. Betulinic acid is obtained by the steps of preparing an extract from the stem bark of *Ziziphus mauritiana* to mediate selective cytotoxic profile against human melanoma in the subject panel of human cancer cell lines, conducting a bioassay-directed fractionation based on the profile of biological activity using cultured human melanoma cells as the monitor, and obtaining betulinic acid.

4 Claims, 5 Drawing Sheets

METHOD AND COMPOSITION FOR SELECTIVELY INHIBITING MELANOMA USING BETALINIC ACID

This invention was made with government support under U01 CA52956 awarded by the National Cancer Institute. The government has certain rights in the invention.

FIELD OF THE INVENTION

This invention relates to compositions and methods of selectively inhibiting tumors and, more particularly, to treating a malignant melanoma using plant-derived compounds.

BACKGROUND OF THE INVENTION

Over the past four decades the incidence of melanoma has been increasing at a higher rate than any other type of cancer. It is now theorized that one in 90 American Caucasians will develop malignant melanoma in their lifetime. While an increasing proportion of melanomas are diagnosed sufficiently early to respond to surgical treatment and achieve a greater than 90% ten-year survival rate, it is estimated that nearly 7,000 individuals suffering from metastatic melanoma will die in the United States this year.

For patients with metastatic melanoma not amenable to surgical extirpation, treatment options are limited. 5-(3,3-dimethyl-1-triazenyl)-1-H-imidazole-4-carboxamide (dacarbazine, DTIC) is the most efficacious single chemotherapeutic agent for melanoma having an overall response rate of 24%. But the duration of response to DTIC is generally quite poor. Combination therapy with other synthetic and recombinant agents, including N,N'-bis(2-chloroethyl)-N-nitrosurea (carmustine, BCNU), cisplatin, tamoxifen, interferon-alpha (INF-α) and interleukin-2 (IL-2), has a higher response rate (e.g., 30-50%) in some trials, but a durable complete response rate is uncommon and toxicity is increased. Sequential chemotherapy has promise, but, clearly, current treatment options for individuals suffering from metastatic melanoma are unsatisfactory.

Various drugs derived from natural products, such as adriamycin (doxorubicin) derivatives, bleomycin, etoposide and vincristine, and their derivatives, have been tested for efficacy against melanoma either as single agents or in combination therapy. However, similar to the synthetic and recombinant compounds, these compounds exhibit low response rates, transient complete responses and high toxicities.

Nonetheless, as demonstrated by known and presently-used cancer chemotherapeutic agents, plant-derived natural products are a proven source of effective drugs. Two such useful natural product drugs are paclitaxel (taxol) and camptothecin. Paclitaxel originally derived from the bark of the Pacific yew tree *Taxus brevifolia* Nutt. (Taxaceae), currently is used for the treatment of refractory or residual ovarian cancer. More recently, clinical trials have been performed to investigate the possible role of paclitaxel in the treatment of metastatic melanoma. As a single agent, taxol displays activity comparable to cisplatin and IL-2. Taxol functions by a unique mode of action, and promotes the polymerization of tubulin. Thus, the antitumor response mediated by taxol is due to its antimitotic activity. The second drug of prominence, camptothecin, was isolated from the stem bark of a Chinese tree, *Camptotheca acuminata* Decaisne (Nyssaceae). Camptothecin also functions by a novel mechanism of action, i.e., the inhibition of topoisomerase I. Phase II trials of a water-soluble camptothecin pro-drug analog, Irinotican (CPT-11), have been completed in Japan against a variety of tumors with response rates ranging from 0% (lymphoma) to 50% (small cell lung). Topotecan, another water-soluble camptothecin analog, currently is undergoing Phase II clinical trials in the United States.

Previous antitumor data from various animal models utilizing betulinic acid have been extremely variable and apparently inconsistent. For example, betulinic acid was reported to demonstrate dose-dependent activity against the Walker 256 murine carcinosarcoma tumor system at dose levels of 300 and 500 mg/kg (milligrams per kilogram) body weight. In contrast, a subsequent report indicated the compound was inactive in the Walker 256 (400 mg/kg) and in the L1210 murine lymphocytic leukemia (200 mg/kg) models. Tests conducted at the National Cancer Institute confirmed these negative data.

Similarly, antitumor activity of betulinic acid in the P-388 murine lymphocyte test system has been suggested. However, activity was not supported by tests conducted by the National Cancer Institute. More recently, betulinic acid was shown to block phorbol ester-induced inflammation and epidermal ornithine decarboxylase accumulation in the mouse ear model. Consistent with these observations, the carcinogenic response in the two-stage mouse skin model was inhibited. Thus, some weak indications of antitumor activity by betulinic acid have been reported, but, until the present invention, no previous reports or data suggested that betulinic acid was useful for the selective control or treatment of human melanoma.

SUMMARY OF THE INVENTION

The present invention is directed to a method and composition for inhibiting tumor growth. The active compound, betulinic acid, is isolated by a method comprising the steps of preparing an extract from the stem bark of *Ziziphus mauritiana* to mediate a selective cytotoxic profile against human melanoma in a subject panel of human cancer cell lines, conducting a bioassay-directed fractionation based on the profile of biological activity using cultured human melanoma cells (MEL-2) as the monitor, and obtaining betulinic acid therefrom as the active compound.

An important aspect of the present invention therefore is to provide a method and composition for inhibiting tumor growth and, particularly, for inhibiting the growth of melanoma using a natural product-derived compound.

Another aspect of the present invention is to provide a treatment method using betulinic acid to prevent the growth or spread of cancerous cells, wherein the betulinic acid is applied in a topical preparation.

Another aspect of the present invention is to overcome the problem of high mammalian toxicity associated with synthetic anticancer agents by using a natural product-derived compound, e.g., betulinic acid.

Still another aspect of the present invention is to overcome the problem of insufficient availability associated with synthetic anticancer agents by utilizing the readily available, naturally-available betulinic acid.

These and other aspects of the present invention will become apparent from the description of the invention disclosed below, which descriptions are intended to limit neither the spirit or scope of the invention but are only offered as illustrations of the preferred embodiments of the invention.

the following cultured human cell lines: A431 (squamous cells), BC-1(breast), COL-2 (colon), HT-1080 (sarcoma), KB, LNCaP (prostate), LU-1 (lung), MEL-2 (melanoma), U373 (glioma) and ZR-75-1 (breast).

TABLE 1

Cytotoxic Activity Profile of the Crude Ethyl Acetate Extract Obtained from *Ziziphus mauritiana*, Betulinic acid, Other Antineoplastic Agents

| Compound | $ED_{50}$ (µg/ml) | | | | | | | | | |
|---|---|---|---|---|---|---|---|---|---|---|
| | A431 | BC-1 | COL-2 | HT-1080 | KB | LNCaP | LU-1 | MEL-2 | U373 | ZR 75-1 |
| *Ziziphus mauritiana* crude extract | >20 | >20 | >20 | 9.5 | >20 | >20 | 5.2 | 3.7 | >20 | 15.8 |
| Betulinic acid | >20 | >20 | >20 | >20 | >20 | >20 | >20 | 2.0 | >20 | >20 |
| Taxol | 0.00 | 0.02 | 0.02 | 0.00 | 0.02 | 0.02 | 0.00 | 0.06 | 0.008 | 0.02 |
| Camptothecin | 0.00 | 0.07 | 0.005 | 0.01 | 0.00 | 0.006 | 0.00 | 0.02 | 0.000 | 0.001 |
| Ellipticine | 0.5 | 0.2 | 0.3 | 1.8 | 0.04 | 0.8 | 0.02 | 0.9 | 1.6 | 0.9 |
| Homoharringtonine | 0.02 | 0.03 | 0.1 | 0.01 | 0.00 | 0.03 | 0.03 | 0.04 | 0.2 | 0.06 |
| Mithramycin A | 0.09 | 0.3 | 0.06 | 1.5 | 0.09 | 0.05 | 0.2 | 1.2 | 0.04 | 0.2 |
| Podophyllotoxin | 0.03 | 0.03 | 0.005 | 0.00 | 0.08 | 0.04 | 0.00 | 0.003 | 0.004 | 0.4 |
| Vinblastine | 0.05 | 0.06 | 0.01 | 0.02 | 0.04 | 0.1 | 0.02 | 0.01 | 1.1 | 0.3 |
| Vincristine | 0.01 | 0.01 | 0.02 | 0.02 | 0.00 | 0.1 | 0.05 | 0.02 | 0.06 | 0.4 |

DETAILED DESCRIPTION OF THE INVENTION

Figure 1:
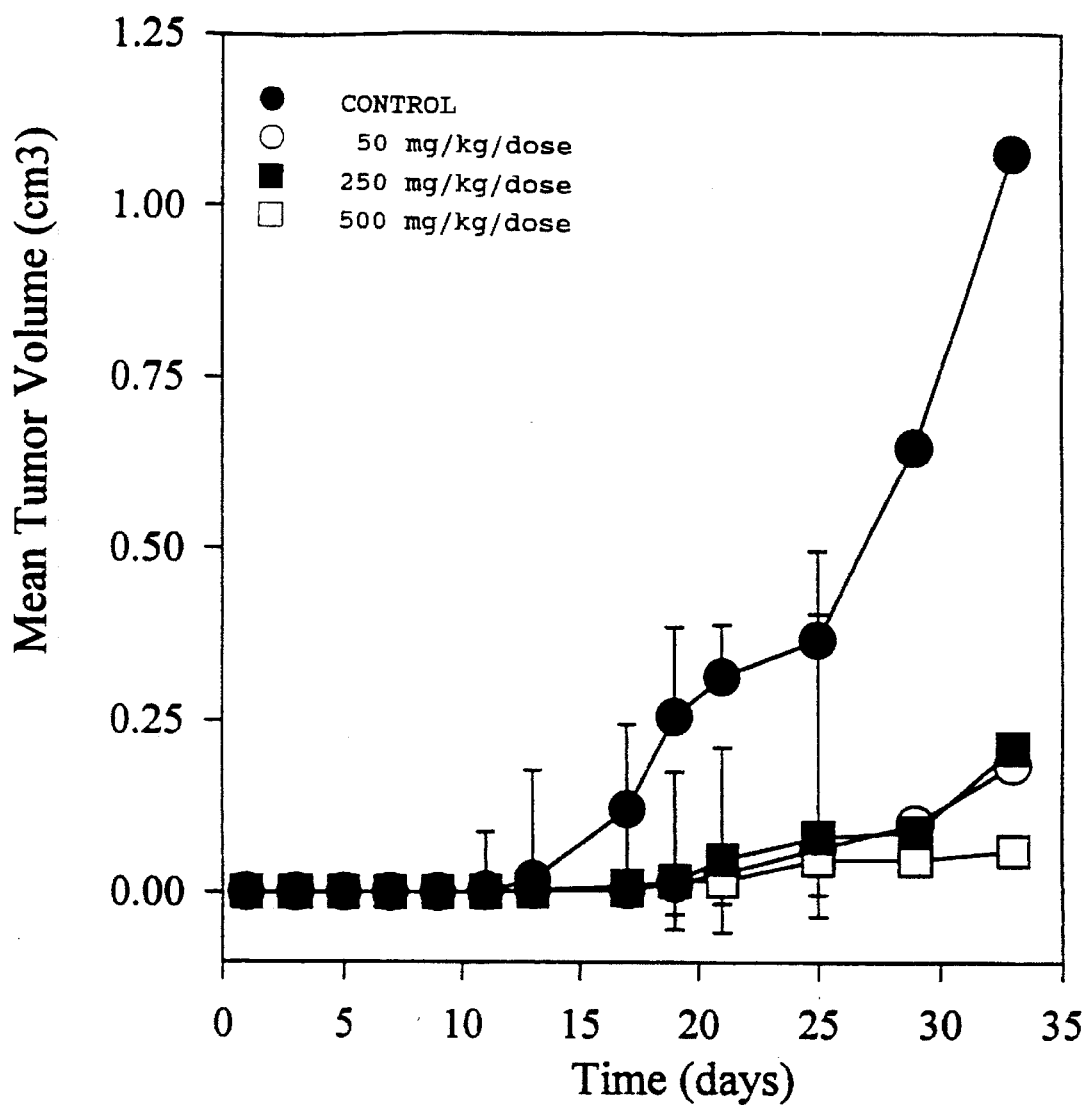
FIG. 1 is a plot of mean tumor volume [in cubic centimeters ($cm^3$)] vs. time for nonestablished MEL-2 tumors in control mice and mice treated with increasing dosages of betulinic acid.

As shown in Table 1, in vitro growth of MEL-2 cells was inhibited by betulinic acid, i.e., an $ED_{50}$ value of about 2 µg/ml. However, none of the other cancer cell lines tested was affected by betulinic acid (i.e., $ED_{50}$ values of greater than 20 µg/ml). Such clearly defined cell-type specificity demonstrated by betulinic acid is both new and unexpected.

For example, as illustrated in Table 1, other known antitumor agents, such as paclitaxel, camptothecin, ellipticine, homoharringtonine, mithramycin A, podopyllotoxin, vinblastine and vincristine, demonstrated relatively intense, nonselective cytotoxic activity with no discernible cell-type selectivity. Moreover, the cytotoxic response mediated by betulinic acid is not exclusively limited to the MEL-2 melanoma cell line. Dose-response studies performed with additional human melanoma cell lines, designated MEL-1, MEL-3 and MEL-4, demonstrated $ED_{50}$ values of 1.1, 3.3 and 4.8 µg/ml, respectively.

In the following Table 1, the extracted betulinic acid and the other pure compounds were tested for cycotoxity against Betulinic acid has the structural formula:

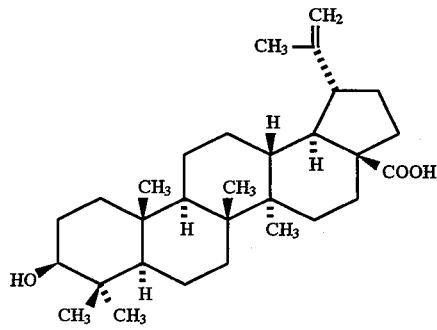

Betulinic acid is fairly widespread in the plant kingdom, and, as a compound frequently encountered, some previous biological activities have been reported.

Betulinic acid was obtained by extracting a sample of air-dried, milled stem bark (450 g) of *Z. mauritiana* with 80% aqueous methanol. The aqueous methanol extract then was partitioned successively with hexane and ethyl acetate to provide hexane, ethyl acetate and aqueous extracts. Among these extracts, the ethyl acetate (13.5 g) extract showed cytotoxic activity against a cultured melanoma cell line (MEL-2) with an $ED_{50}$ of 3.7 µg/ml. The ethyl acetate extract was chromatographed on a silica gel column using hexane-ethyl acetate (4:1 to 1:4) as eluent to give 10 fractions. Fractions 3 and 4 were combined and subjected to further fractionation to afford an active fraction (fraction 16) showing a major single spot by thin-layer chromatography [$R_f$ 0.67: $CHCl_3$:MeOH (chloroform:methanol) (10:1)], which yielded 72 mg of colorless needles after repeated crystallization from methanol (overall yield from dried plant material: 0.016% w/w).

As confirmed by the data summarized in Table 1, betulinic acid has been reported as noncytotoxic with respect to cultured KB cells. Cytotoxicity of the crude extracts and purified compounds was determined in a number of cultured human cancer cell lines. Table 1 sets forth the various types of cancer cells evaluated. The cells were cultured in appropriate media and under standard conditions. To maintain logarithmic growth, the media were changed 24 hours prior to cytotoxic assays. On the day of the assay, the cells were harvested by trypsinization, counted, diluted in media, and added to 96-well plates containing test compounds dissolved in DMSO; the final DMSO concentration was 0.05%.

The plates were incubated for three days. Following the incubation period, the cells were fixed and stained with sulforhodamine B (SRB) dye. The bound dye was liberated with Tris base, and the $OD_{515}$ was measured on an ELISA reader. The growth of the betulinic acid-treated cells was determined by the $OD_{515}$ values, and the growth was compared to the $OD_{515}$ values of DMSO-treated control cells. Dose response studies were performed to generate $ED_{50}$ values.

The isolated active compound, betulinic acid ($ED_{50}$ of 2.0 μg/ml for MEL-2), has a molecular formula of $C_{30}H_{48}O_3$, as determined by high-resolution mass spectral analysis, a melting point range of 292°–293° C. (decomposition). The literature melting point range for betulinic acid is 290°–293° C. A mixed melting point range with a known sample of betulinic acid was not depressed. The optical rotation of the compound was measured as +7.3° (c=1.2; pyridine) (lit. +7.5°). The identity of the isolated compound as betulinic acid was confirmed by comparing the above physical properties, as well as $^1$H-nmr, $^{13}$C-nmr and mass spectral data of the isolated compound, with physical data and spectra of a known sample of betulinic acid as reported in the literature.

To test the in vivo ability of betulinic acid to serve as an antineoplastic agent against malignant melanoma, a series of studies was performed with athymic (nude) mice injected subcutaneously with human melanoma cells (MEL-2). The initial study investigated the activity of betulinic acid against unestablished tumors. Treatment with betulinic acid began on day 1, i.e., 24 hours, following tumor cell injection. At doses of 50, 250, and 500 mg/kg (milligram per kilogram) body weight, betulinic acid demonstrated effective inhibition of tumor growth with p values of 0.001 for each dose versus a control (FIG. 1).

In particular, the data plotted in FIG. 1 was derived from experiments wherein four week old athymic mice were injected subcutaneously in the right flank with $3.0 \times 10^8$ UISO MEL-2 cells. UISO MEL-2 is a cell line derived from metastatic melanoma from human pleural fluid. Drug treatment was initiated on the day following tumor cell injection and continued every fourth day for a total of six doses. Four control animals received 0.5 ml intraperitoneal (IP) of PVP control solution, while treated animals (4 per group) received 50, 250 or 500 mg/kg/dose IP betulinic acid/PVP in deionized $H_2O$. Betulinic acid was coprecipitated with PVP to increase solubility and bioavailability. The mice were weighed, and the tumors measured with a micrometer every other day throughout the study. All animals were sacrificed and autopsied on day 33, when the mean tumor volume in the control animals was approximately one $cm^3$.

There was greater inhibition of tumor growth at the highest dose of betulinic acid versus the lowest dose (p=0.04). Toxicity was not associated with the betulinic acid treatment because toxicity is indicated by loss of body weight or other forms of acute toxicity. No weight loss was observed.

Figure 2:
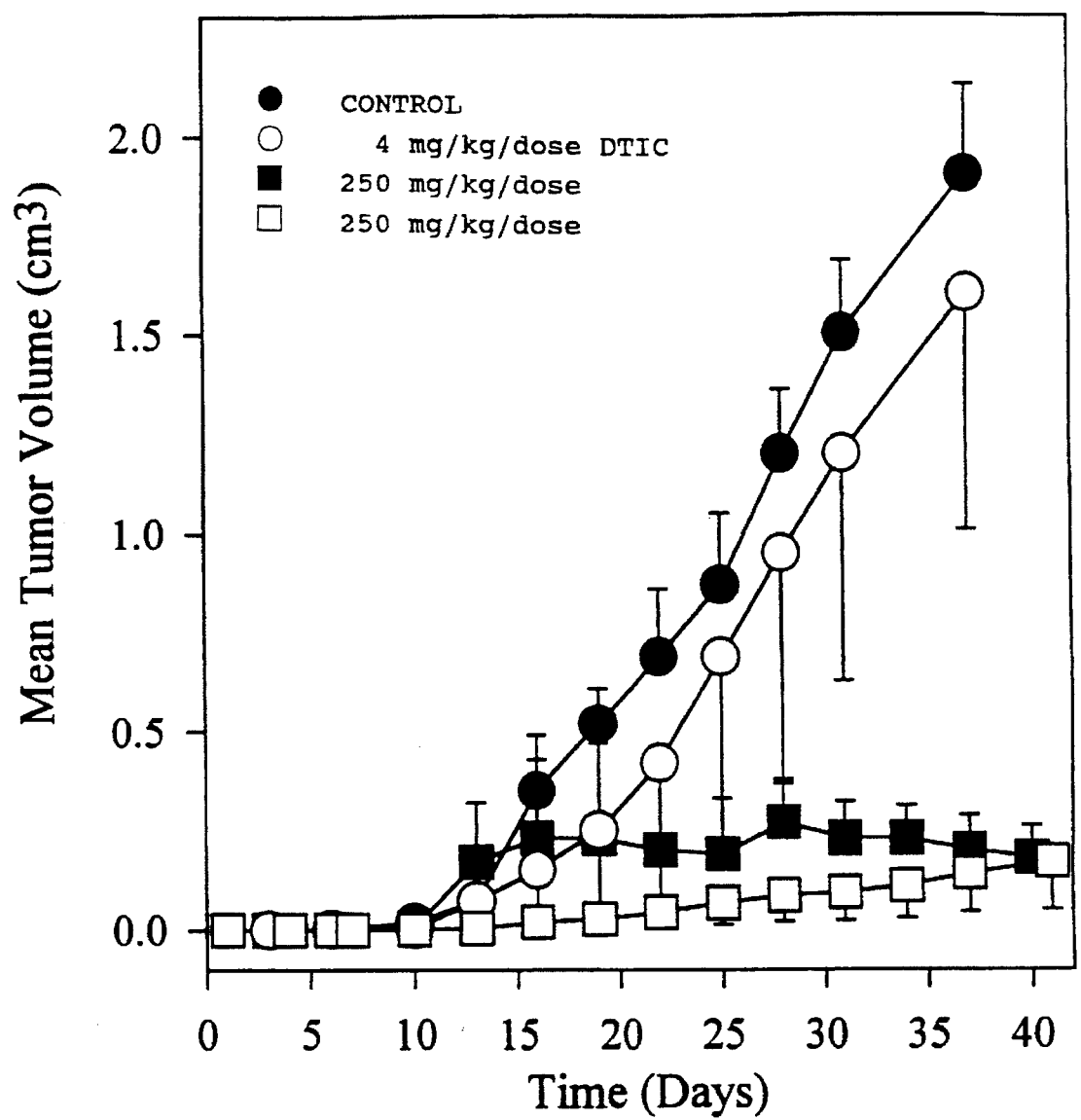
FIG. 2 is a plot of mean tumor volume (in $cm^3$) vs. time for established MEL-2 tumors in control mice and mice treated with DTIC or betulinic acid.

Next, in vivo testing of betulinic acid was performed on established melanomas. In this study, treatment was withheld until day 13, by which time a palpable tumor mass was present in all mice. As illustrated in FIG. 2, under these conditions betulinic acid successfully abrogated tumor growth (p=0.0001). Furthermore, tumor growth did not parallel that of the control (untreated) group even 14 days after the termination of treatment.

In particular, with respect to FIG. 2, four-week-old athymic mice were injected with $5 \times 10^8$ MEL-2 cells subcutaneously in the right flank. Four treatment groups of five mice each were studied. In one group, the mice received 250 mg/kg/dose of IP betulinic acid/PVP every third day for six total doses initiated the day following tumor cell injection. The control group received 0.5 ml IP saline. A DTIC treatment group received 4 mg/kg/dose IP DTIC every third day from day 13 to day 28 of the study. The betulinic acid treatment group received 250 mg/kg/dose IP betulinic acid/PVP every third day from day 13 to day 27. The control and DTIC-treated mice were sacrificed and autopsied on day 36 due to their large tumor burden. The remaining mice were sacrificed and autopsied on day 41.

As illustrated in FIG. 2, the efficacy of betulinic acid also was compared to DTIC, which is clinically available for the treatment of metastatic melanoma. The dose of DTIC, which is limited by toxicity, was selected to be equivalent to that administered to human patients. Tumor growth in the betulinic acid-treated group was significantly less than that observed in the DTIC-treated animals (p =0.0001). Compared to controls, DTIC produced a significant, but less pronounced, reduction in tumor growth, with a p value of 0.01. A fourth group in this study was treated with a schedule similar to that in the initial study. Under these conditions, betulinic acid, as demonstrated before, significantly inhibited tumor development (p =0.0001) and caused a prolonged reduction in tumor growth of up to three weeks following treatment termination.

Figure 4:
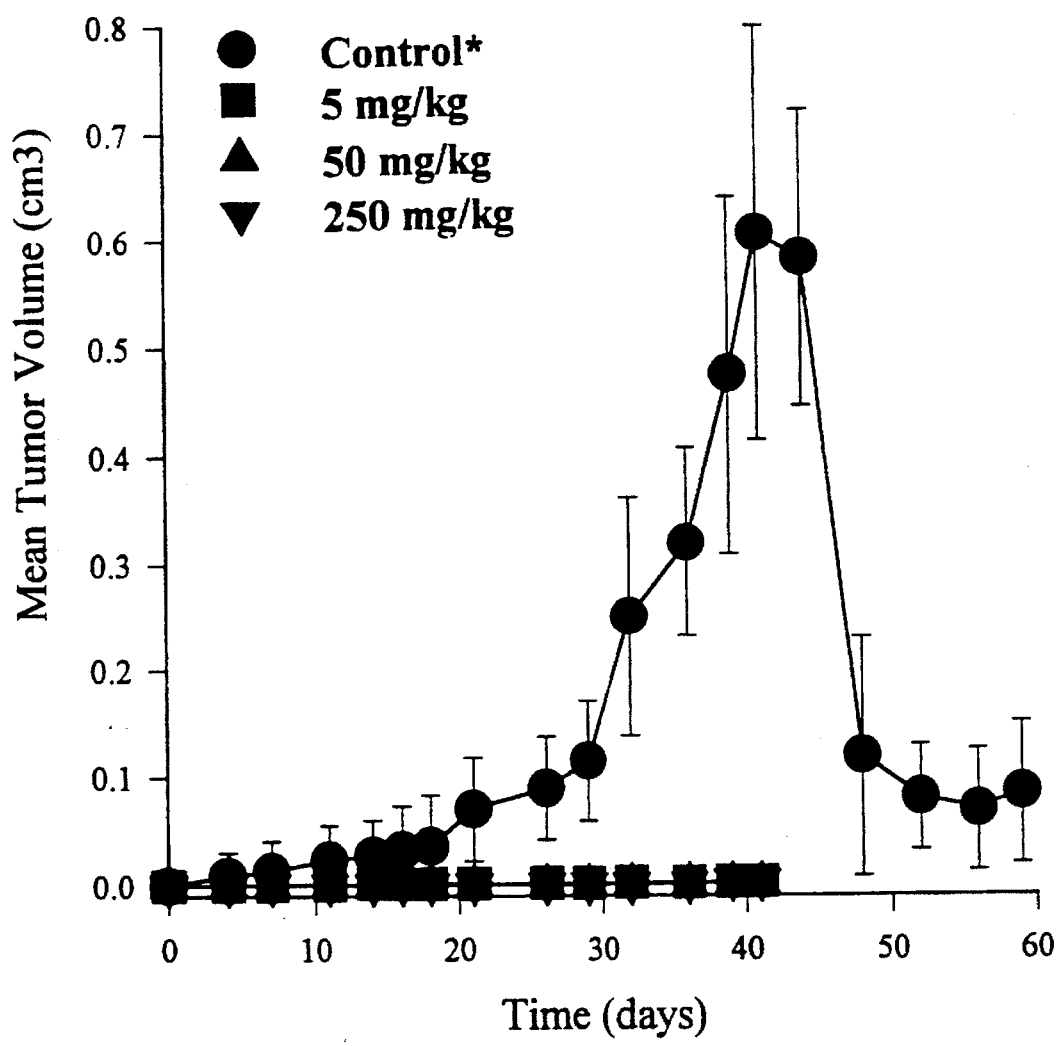
FIGS. 4 and 5 are plots of mean tumor volume ($cm^3$) vs. time for established and nonestablished MEL-1 tumors in control mice and mice treated with increasing doses of betulinic acid.
Figure 5:
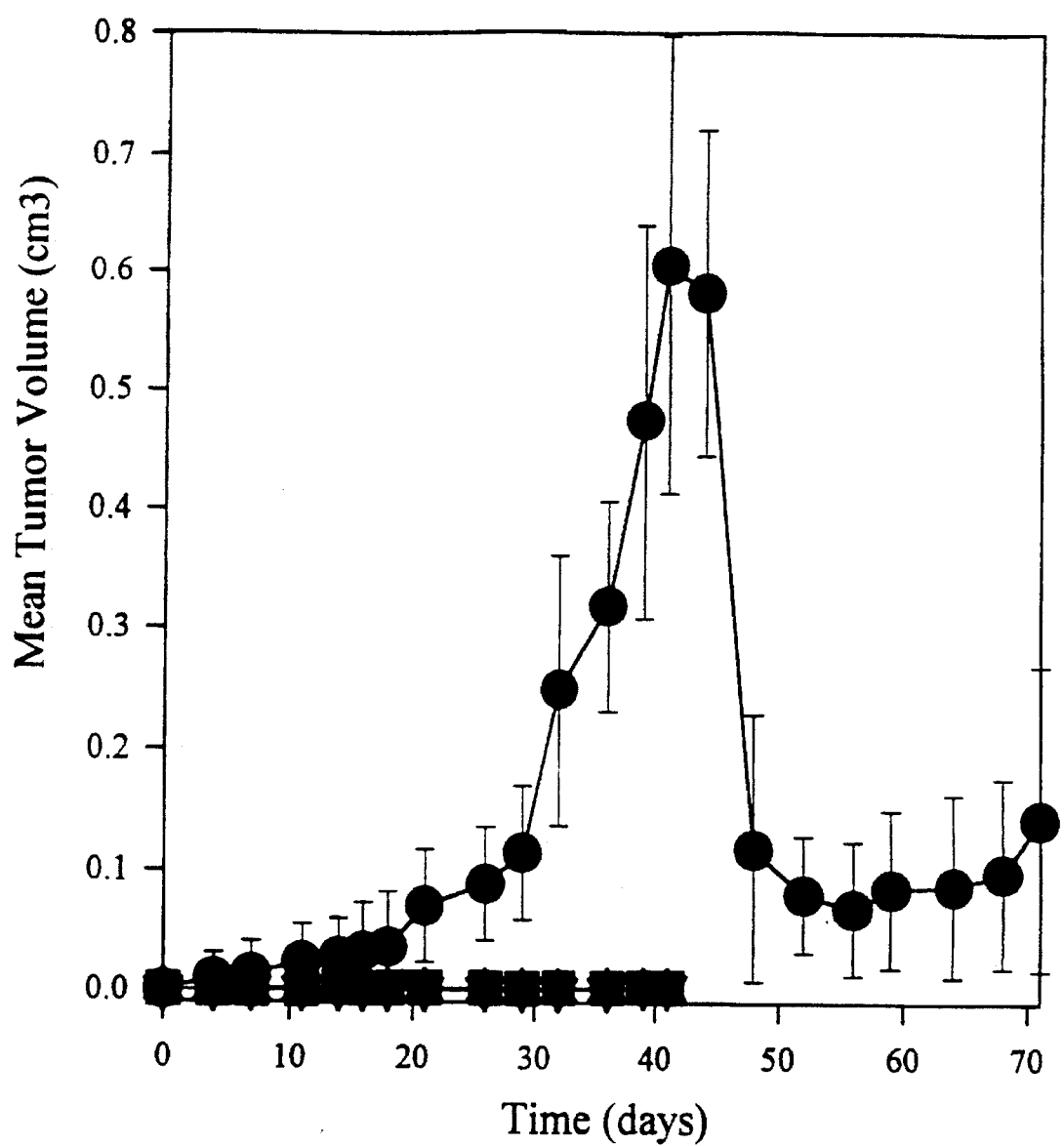

FIGS. 4 and 5 illustrate that betulinic acid also showed activity against MEL-1 cells. In particular, with respect to FIGS. 4 and 5, four week old athymic mice were injected subcutaneously in the right flank with $5.0 \times 10^8$ UISO MEL-1 cells. Drug treatment was initiated on the day following tumor cell injection and continued every fourth day for a total of six doses. Four control animals received 0.5 ml intraperitoneal (IP) saline, while treated animals (4 per group) received 5, 50 or 250 mg/kg/dose IP betulinic acid/PVP in dd $H_2O$. The mice were weighed, and tumors were measured with a micrometer every third day throughout the study. Treated animals were sacrificed and autopsied on day 41, when the mean tumor volume in the control mice was approximately 0.5 $cm^3$. The control mice then received six doses of 50 mg/kg every fourth day beginning day 41 and were sacrificed and autopsied on day 71.

The results illustrated in FIGS. 4 and 5 with respect to MEL-1 cells were similar to the results illustrated in FIGS. 1 and 2. Betulinic acid therefore is active both against MEL-1 and MEL-2 cells.

The mechanism by which antitumor agents mediated their activity is of great theoretical and clinical importance. Therefore, the mode of action by which betulinic acid mediates the melanoma-specific effect was investigated. Visual inspection of melanoma cells treated with betulinic acid revealed numerous surface blebs. This observation, as opposed to cellular membrane collapse, suggested the induction of apoptosis. One of the most common molecular and cellular anatomical markers of apoptosis is the formation of "DNA ladders", which correspond to the products of random endonucleolytic digestion of inter-nucleosomal DNA. Although recent studies have shown that a lack of DNA laddering does not necessarily indicate a failure to undergo apoptosis, double-strand DNA scission that yields a fragment of about 50 kilobase pairs (Kbp) has been shown to consistently correlate with induction of apoptosis by various treatments in a variety of cell lines. Thus, generation of the 50 Kbp fragment is a reliable and general indicator of apoptosis. Generation of the fragment occurs upstream of the process leading to DNA ladders and represents a key early step in the commitment to apoptosis.

Therefore, an important feature of the present invention is a method of analyzing and quantifying the formation of the 50 Kbp fragment as a biomarker for induction of apoptosis in human cancer cell lines. This method comprises treatment of cells in culture, followed by analysis of the total cellular DNA content using agarose field-inversion gel electrophoresis. Under these conditions, the 50 Kbp fragment is resolved as a diffuse band. The fraction of the total cellular DNA represented by the 50 Kbp fragment is determined by densitometry on the contour of this band.

To investigate the ability of betulinic acid to induce apoptosis, the above-described method was adapted for use with the MEL-2 cell line. As shown in FIG. 3A, time-dependent formation of a 50 Kbp DNA fragment was induced by betulinic acid with MEL-2 cells. Induction was at a maximum after a 56 hour treatment period. After this time period, a decline in the relative amount of the 50 Kbp fragment was observed, probably due to internal degradation. Also observed in the agarose gel were DNA fragments of about 146 and about 194 Kbp, which are theorized to be precursors in the process leading to the formation of the 50 Kbp fragment. Additionally, the induction of apoptosis (50 Kbp fragment) mediated by betulinic acid was dose-dependent (FIG. 3B), and the $ED_{50}$ value (about 1.5 µg/ml) observed in the apoptotic response closely approximated the $ED_{50}$ value previously determined for the cytotoxic response (Table 1).

With further respect to FIG. 3A, cultured MEL-2 cells ($10^6$ cells inoculated per 25 cm$^2$ flask) were treated with 2 g/ml betulinic acid (200 µg/ml DMSO, diluted 1:100 in media) for 24, 32, 48, 56 and 72 hours. After the treatment, the cells were harvested, collected by centrifugation, then snap frozen in liquid nitrogen for subsequent analysis. Samples were analyzed on a 1% agarose gel in a Hoefer HE100 SuperSub apparatus cooled to 10° C. by a circulating water bath. The electrode buffer was 0.5× TBE buffer containing 0.25 µg/ml ethidium bromide and was circulated during electrophoresis. Each gel included 20 µL Sigma Pulse Marker 0.1–200 Kbp DNA size markers. Prior to sample loading, 50 µL 2% SDS was added to each sample well. Each sample tube was rapidly thawed, then the pelleted cells were immediately transferred in a volume about 50 µL to the well containing SDS. Each well then was overlaid with molten LMP agarose, which was allowed to gel prior to placing the gel tray in the SuperSub apparatus.

Electrophoresis was performed at 172 volts for a total of 18 hours using two sequential field inversion programs with pulse ramping. The DNA/ethidium bromide fluorescence was excited on a UV transilluminator and photographed using Polaroid type 55 P/N film. The negative was analyzed using a PDI scanning densitometer and Quantity One software. The intensity of the 50 Kbp fragment was determined by measuring the contour optical density (OD×mm$^2$) as a percent of the total optical density in the sample lane, including the sample well. The decrease in the 50 Kbp band definition caused by internal degradation, and does not represent a reversal of the process.

Figure 3B:
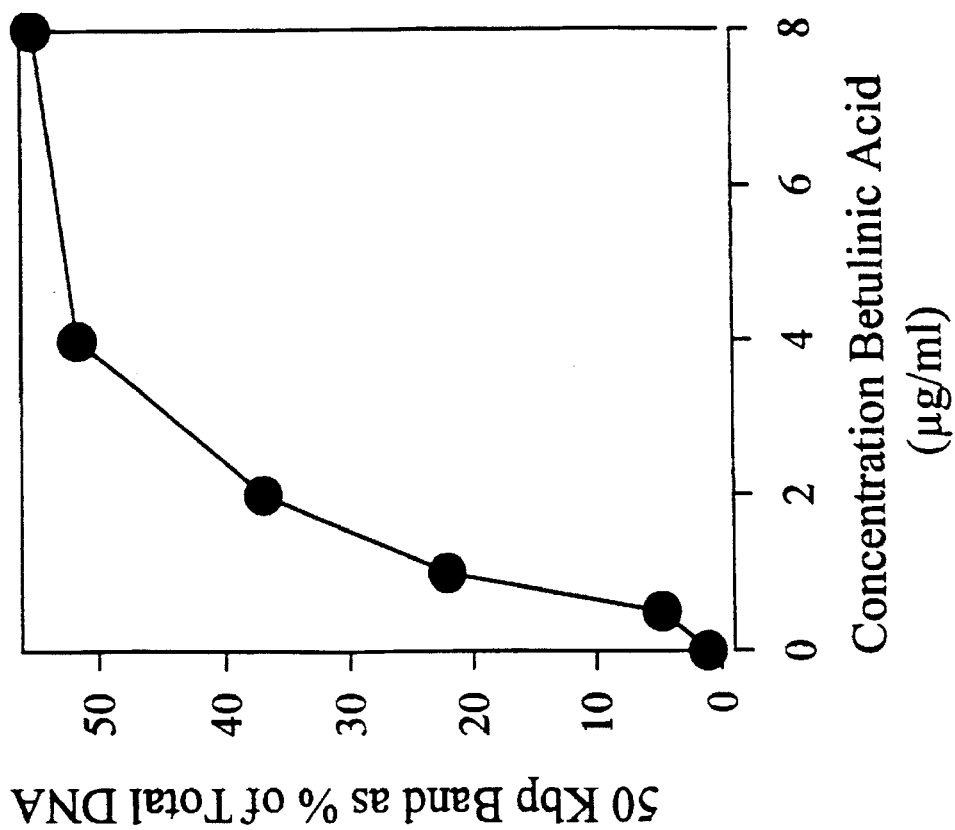
FIG. 3(B) is a plot of the 50 Kbp band as total DNA versus concentration of betulinic acid (µg/ml)
Figure 3A:
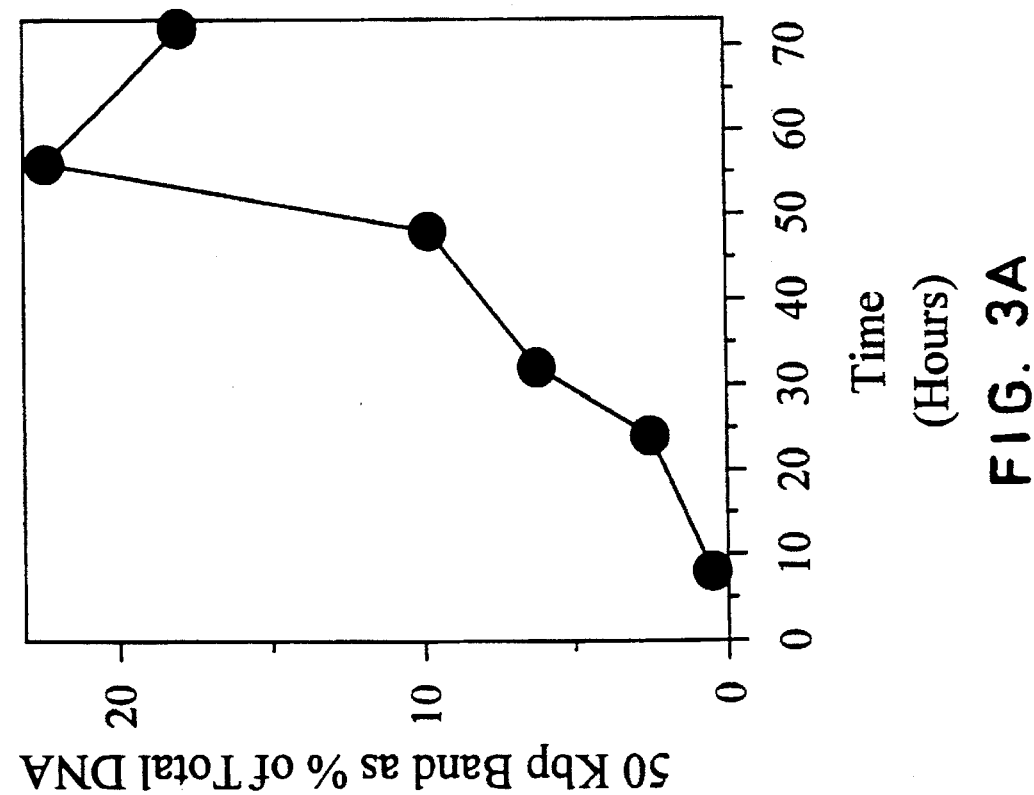
FIG. 3(A) is a plot of the 50 Kbp (kilobase pairs) band as % total DNA v. time for treatment of MEL-2 cells with 2 µg/ml (micrograms per milliliter) betulinic acid.

With further respect to FIG. 3B, cultured MEL-2 cells were treated for 56 hours with the following concentrations of betulinic acid: 0, 0.1, 1.0, 2.0, 4.0 and 8.0 µg/ml. The cells were harvested and apoptosis measured as described for FIG. 3A. The experiment was repeated and a similar dose-response curve was observed (data not shown).

These data suggest a causal relationship, and it is theorized that betulinic acid-mediated apoptosis is responsible for the antitumor effect observed with athymic mice. Time-course experiments with human lymphocytes treated in the same manner with betulinic acid at concentrations of 2 and 20 µg/ml did not demonstrate formation of the 50 Kbp fragment (data not shown) indicating the specificity and possible safety of the test compound.

Taking into account a unique in vitro cytotoxicity profile, a significant in vivo activity, and mode of action, betulinic acid is an exceptionally attractive compound for treating human melanoma. Betulinic acid also is relatively innocuous toxicitywise, as evidenced by repeatedly administering 500 mg/kg doses of betulinic acid without causing acute signs of toxicity or a decrease in body weight. Betulinic acid was previously found to be inactive in a Hippocratic screen at 200 and 400 mg/kg doses.

Betulinic acid also does not suffer from the drawback of scarcity. Betulinic acid is a common triterpene available from many species throughout the plant kingdom. More importantly, a betulinic acid analog, betulin, is the major constituent of white-barked birch species (up to 22% yield), and betulin is easily oxidized to betulinic acid.

In addition to betulinic acid, betulinic acid derivatives can be used in a topically-applied composition to selectively treat and inhibit a melanoma. Betulinic acid derivatives include, but are not limited to esters of betulinic acid, such as betulinic acid esterified with an alcohol having one to sixteen carbon atoms, or amides of betulinic acid, such as betulinic acid reacted with ammonia or a primary or secondary amine having alkyl groups containing one to ten carbon atoms.

Another betulinic acid derivative is a salt of betulinic acid. Exemplary, but nonlimiting, betulinic acid salts include an alkali metal salt, like a sodium or potassium salt; an alkaline earth metal salt, like a calcium or magnesium salt; an ammonium or alkylammonium salt, wherein the alkylammonium cation has one to three alkyl groups and each alkyl group independently has one to four carbon atoms; or transition metal salt.

Other betulinic acid derivatives also can be used in the composition and method of the present invention. One other derivative is the aldehyde corresponding to betulinic acid or betulin. Another derivative is acetylated betulinic acid, wherein an acetyl group is positioned at the hydroxyl group of betulinic acid.

What we claim is:

1. A method of inhibiting growth of a melanoma comprising topically applying a therapeutically-effective amount of betulinic acid to the melanoma.

2. A method of inhibiting growth of a melanoma comprising topically applying a therapeutically-effective amount of a betulinic acid derivative to the melanoma, said betulinic acid derivative selected from the group consisting of a salt of betulinic acid; acetylated betulinic acid; a $C_1$–$C_{16}$ ester of betulinic acid; an amide of betulinic acid wherein the amide group is a residuum of ammonia, a primary amine or a secondary amine, wherein the primary or secondary amine has alkyl groups having one to ten carbon atoms; and an aldehyde corresponding to betulinic acid.

3. A method of inhibiting growth of a melanoma comprising topically applying, to an individual in need of such treatment, a therapeutically-effective amount of betulinic acid.

4. A method of inhibiting growth of a melanoma comprising topically applying, to an individual in need of such treatment, a therapeutically-effective amount of a betulinic acid derivative selected from the group consisting of a salt of betulinic acid; acetylated betulinic acid; a $C_1$–$C_{16}$ ester of betulinic acid; an amide of betulinic acid wherein the amide group is a residuum of ammonia, a primary amine or a secondary amine, wherein the primary or secondary amine has alkyl groups having one to ten carbon atoms; and an aldehyde corresponding to betulinic acid.

* * * * *

UNITED STATES PATENT AND TRADEMARK OFFICE
CERTIFICATE OF CORRECTION

PATENT NO. : 5,658,947

DATED : August 19, 1997

INVENTOR(S) : Tapas K. DasGupta et al.

It is certified that error appears in the above-identified patent and that said Letters Patent is hereby corrected as shown below:

On the title page, and column 1,

In the title, "BETALINIC" should be --BETULINIC--.

Column 6, line 2, "5 x 108" should be --$5 \times 10^8$--.

Signed and Sealed this

Eleventh Day of November, 1997

Attest:

BRUCE LEHMAN

Attesting Officer

Commissioner of Patents and Trademarks